(12) United States Patent
Zhang et al.

(10) Patent No.: US 12,329,898 B1
(45) Date of Patent: Jun. 17, 2025

(54) BUTTON ASSEMBLY FOR INHALER, AND INHALER

(71) Applicant: SUZHOU SINGMED MEDICAL DEVICE SCIENCE AND TECHNOLOGY LTD., Suzhou (CN)

(72) Inventors: Fei Zhang, Jiangsu Province (CN); Xiaoyuan Sun, Jiangsu Province (CN); Guangtao Zhao, Jiangsu Province (CN)

(73) Assignee: SUZHOU SINGMED MEDICAL DEVICE SCIENCE AND TECHNOLOGY LTD., Jiangsu Province (CN)

( * ) Notice: Subject to any disclaimer, the term of this patent is extended or adjusted under 35 U.S.C. 154(b) by 0 days.

(21) Appl. No.: 19/037,930

(22) Filed: Jan. 27, 2025

Related U.S. Application Data

(63) Continuation-in-part of application No. PCT/CN2024/139989, filed on Dec. 17, 2024.

(30) Foreign Application Priority Data

Jul. 3, 2024 (CN) .......................... 202410885061.4

(51) Int. Cl.
*A61M 15/00* (2006.01)
*A61M 11/02* (2006.01)

(52) U.S. Cl.
CPC ........ *A61M 15/0001* (2014.02); *A61M 11/02* (2013.01); *A61M 15/009* (2013.01); *A61M 2202/0468* (2013.01); *A61M 2205/0216* (2013.01)

(58) Field of Classification Search
CPC ................. A61M 11/00; A61M 11/08; A61M 15/00–0001; A61M 15/009; A61M 2205/27; A61M 2205/276
See application file for complete search history.

(56) References Cited

U.S. PATENT DOCUMENTS

| | | | | |
|---|---|---|---|---|
| 5,347,998 A | * | 9/1994 | Hodson | A61M 15/0095 128/200.23 |
| 2011/0114089 A1 | * | 5/2011 | Andersen | A61M 15/0081 128/200.23 |
| 2018/0221601 A1 | * | 8/2018 | Meshberg | A61M 15/009 |
| 2023/0103823 A1 | * | 4/2023 | Hausmann | B05B 11/1091 222/401 |

FOREIGN PATENT DOCUMENTS

| | | |
|---|---|---|
| CN | 1203533 A | 12/1998 |
| CN | 116328111 A | 6/2023 |
| CN | 117548251 A | 2/2024 |
| CN | 220632721 U | 3/2024 |
| CN | 118594803 A | 9/2024 |
| CN | 118807039 A | 10/2024 |
| CN | 118807040 A | 10/2024 |

\* cited by examiner

*Primary Examiner* — Rachel T Sippel
(74) *Attorney, Agent, or Firm* — FisherBroyles, LLP; John K. Shimmick

(57) ABSTRACT

A button assembly for an inhaler is provided. The button assembly includes: a button body; an elastic member having a first end and a second end relative to the first end, wherein the first end is coupled to the button body, and the second end is used to be coupled to a housing of the inhaler; and at least one arm having a proximal end coupled to the button body, wherein if a distal end of the at least one arm relative to the proximal end is close to the housing of the inhaler, the button body stretches the elastic member.

20 Claims, 15 Drawing Sheets

BUTTON ASSEMBLY FOR INHALER, AND INHALER

CROSS REFERENCE TO RELATED APPLICATIONS

The present application is a continuation in part of the international application No. PCT/CN2024/139989, filed on Dec. 17, 2024, and the international application claims priority of Chinese Patent Application No. 202410885061.4, filed on Jul. 3, 2024, and entitled "TRIGGER ASSEMBLY FOR INHALER, AND INHALER", the entire contents of which being incorporated herein by reference.

TECHNICAL FIELD

The present disclosure relates to the field of medical devices, and in particular to a button assembly for an inhaler and an inhaler.

BACKGROUND

An inhaler can nebulize a liquid (e.g., a liquid drug) into droplets. In the related art, a container of an inhaler contains a liquid to be nebulized or sprayed, and during a movement travel of the container relative to a spraying assembly, the liquid in the container may be nebulized, and the nebulized liquid is sprayed from a nozzle of the spray assembly.

SUMMARY OF THE INVENTION

The present disclosure provides a button assembly for an inhaler and an inhaler.

According to a first aspect of the present disclosure, a button assembly for an inhaler is provided, the button assembly including: a button body; an elastic member having a first end and a second end opposite the first end, wherein the first end is coupled to the button body, and the second end is used to be coupled to a housing of the inhaler; and a first arm and a second arm, respective proximal ends of the first arm and the second arm being coupled to the button body, wherein if respective distal ends, opposite the proximal ends, of the first arm and the second arm being away from each other, the button body presses the elastic member, and if the respective distal ends of the first arm and the second arm being close to each other, the button body stretches the elastic member.

According to a second aspect of the present disclosure, an inhaler is provided, the inhaler including: a spray assembly; and a button assembly according to the first aspect of the present disclosure, the button assembly being configured to be pressed to actuate the spray assembly to spray a liquid.

The above description is merely a summary of the technical solutions of the present application. To make the technical means of the present application more clearly understood and implemented according to the contents of the specification, and to make the above and other objectives, features, and advantages of the present application more obvious and comprehensible, the embodiments of the present application are described in detail below.

BRIEF DESCRIPTION OF THE DRAWINGS

More details, features, and advantages of the present disclosure are disclosed in the following description of example embodiments with reference to the accompanying drawings, in which.

DETAILED DESCRIPTION

In the present disclosure, unless otherwise stated, the terms "first", "second", etc., used to describe various elements are not intended to limit the positional, temporal or importance relationship of these elements, but rather only to distinguish one component from another. In some examples, a first element and a second element may refer to a same instance of the element, and in some cases, based on contextual descriptions, the first element and the second element may also refer to different instances.

In the scope of the present disclosure, an "inhaler" refers to a device for nebulizing a liquid. Generally, the inhaler is used to nebulize a fluid (e.g., a liquid drug or similar fluid) and spray the nebulized fluid to the mouth or nose of a user (e.g., a patient).

In the related art, a container of an inhaler contains a liquid to be nebulized or sprayed, and during a movement travel of the container relative to a spraying assembly, the liquid in the container may be nebulized, and the nebulized liquid is sprayed from a nozzle of the spray assembly. However, the button assembly for the inhaler in the related art is generally roughly made, and the feedback provided to the user by a button is unstable. Therefore, there is a need to provide an inhaler with an improved button assembly.

In view of this, the present disclosure provides a button assembly for an inhaler and an inhaler. In the scope of the present disclosure, the button assembly can be mounted into an inhaler and can be linked with a spray assembly of the inhaler to actuate the spray assembly to perform a spraying action.

In the scope of the present disclosure, a "preloaded position" of the spray assembly may refer to a position in which a liquid in the inhaler is loaded to be ready to be sprayed outwards (e.g., loaded from a tank into a pumping chamber). In this position, if there is no external force to trigger, the inhaler cannot carry out spraying autonomously, but only by manual operation (such as pressing the button assembly according to the present disclosure) can the spray assembly be triggered to cause the spray assembly to restore from the "preloaded position" to a "triggered position", that is, the liquid in the inhaler is switched from a loaded-to-prespray state to an nebulized-to-spray state. In the "triggered position", the inhaler can be operated (e.g. screwed) again to switch to the "preloaded position", so the "triggered position" may also be referred to as an initial position.

Figure 1:
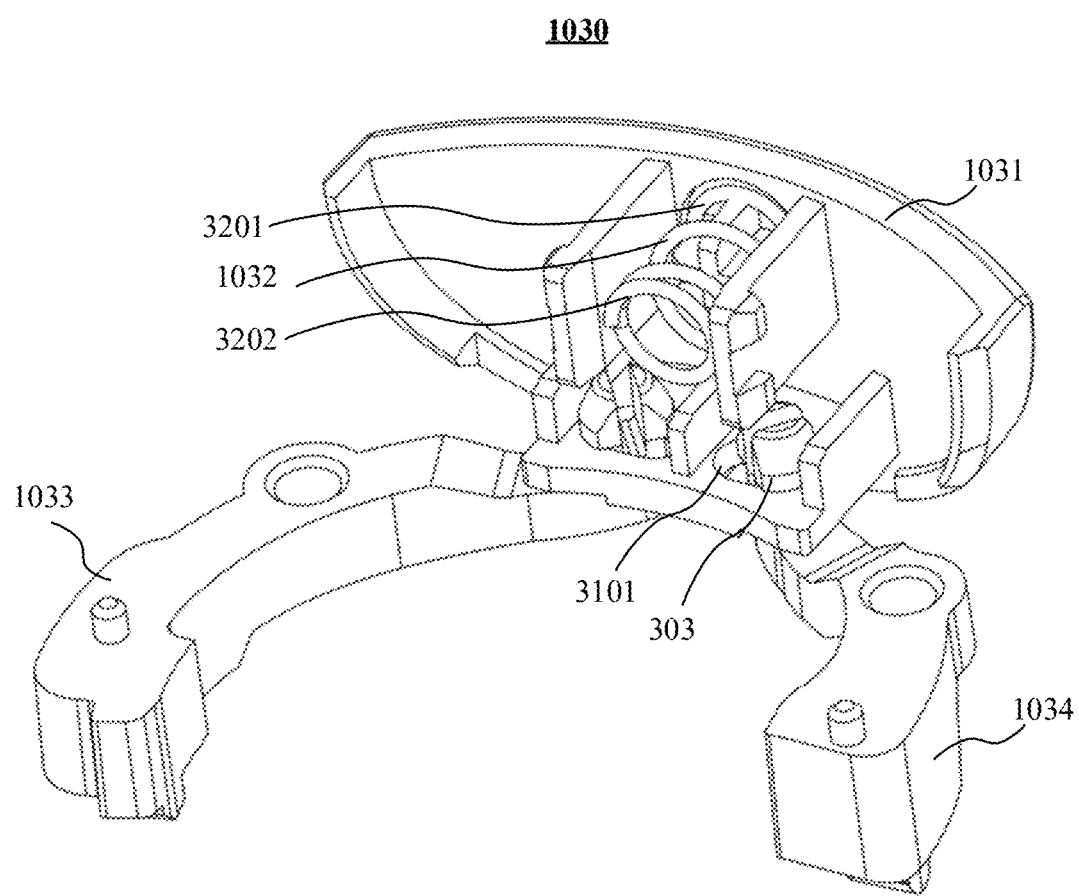
FIG. 1 is a schematic diagram illustrating a button assembly for an inhaler according to an example embodiment.
Figure 2:
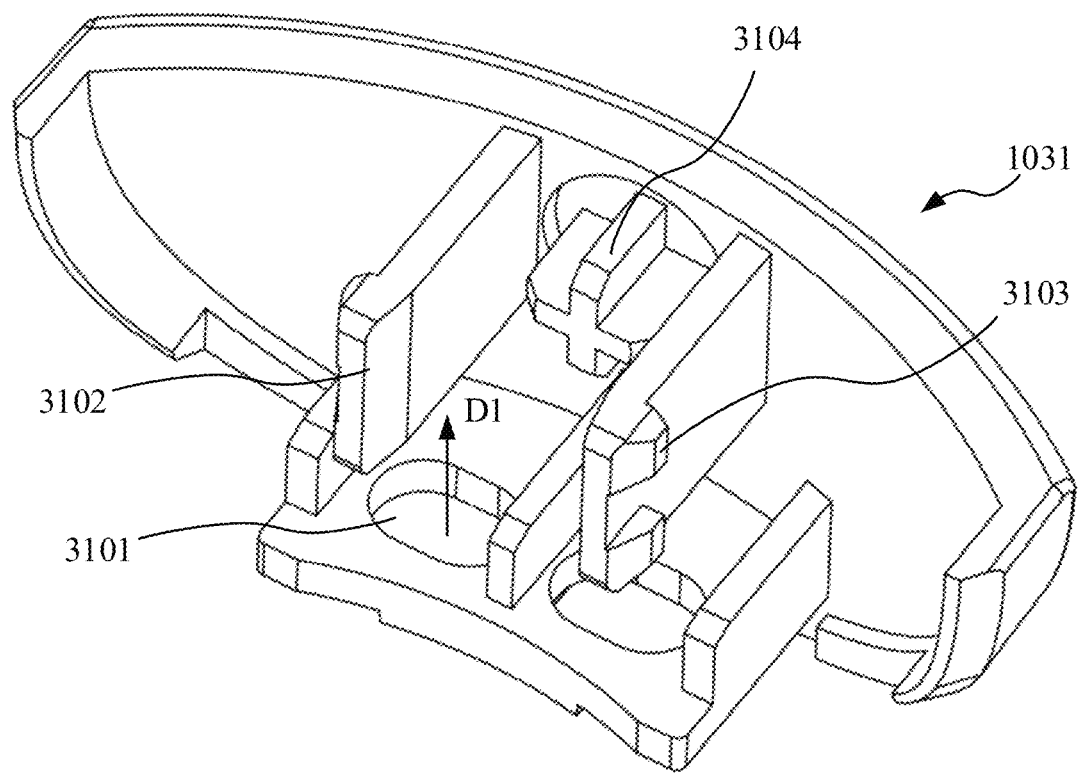
FIG. 2 is a schematic diagram of a button body of the button assembly of FIG. 1.
Figure 3:
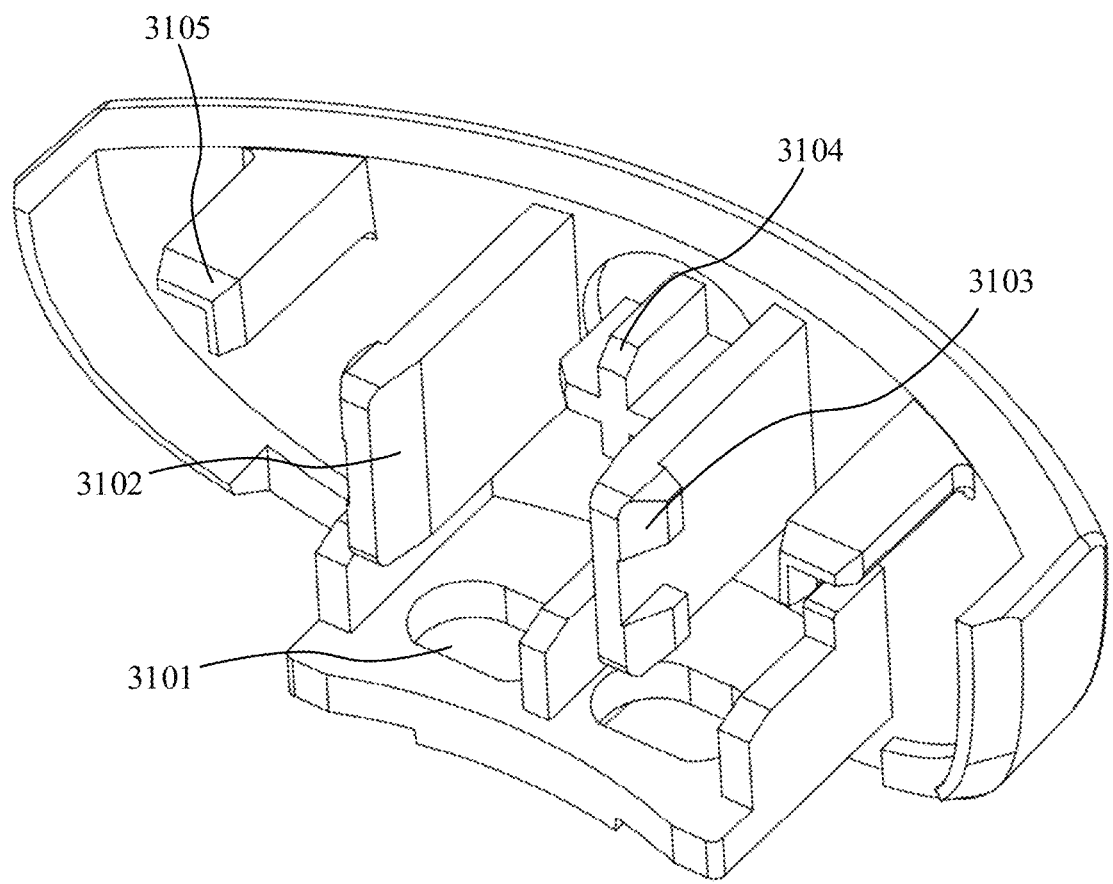
FIG. 3 is a schematic diagram of another embodiment of the button body of the button assembly of FIG. 2.
Figure 4:
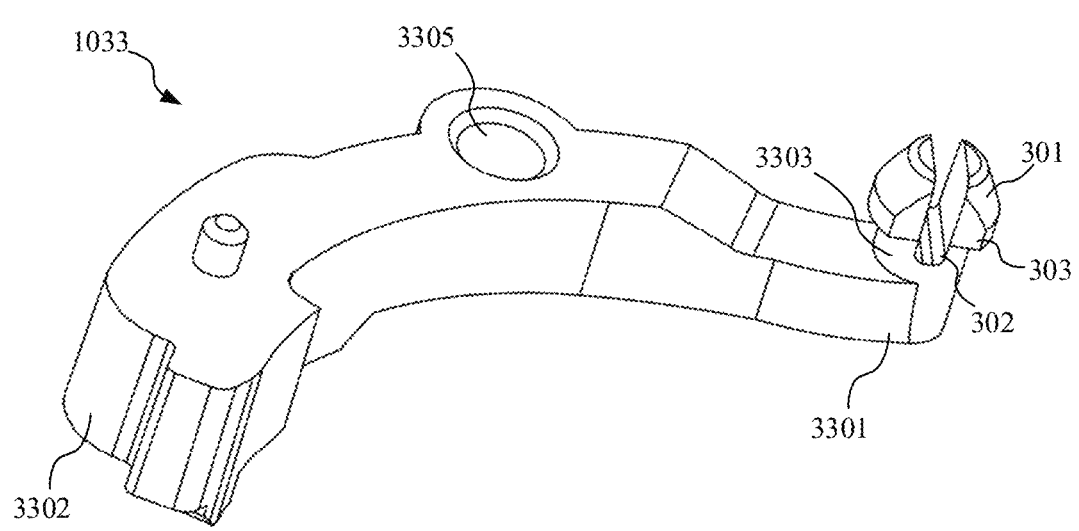
FIGS. 4 and 5 are schematic diagrams of a first arm and a second arm of FIG. 1, respectively.
Figure 5:
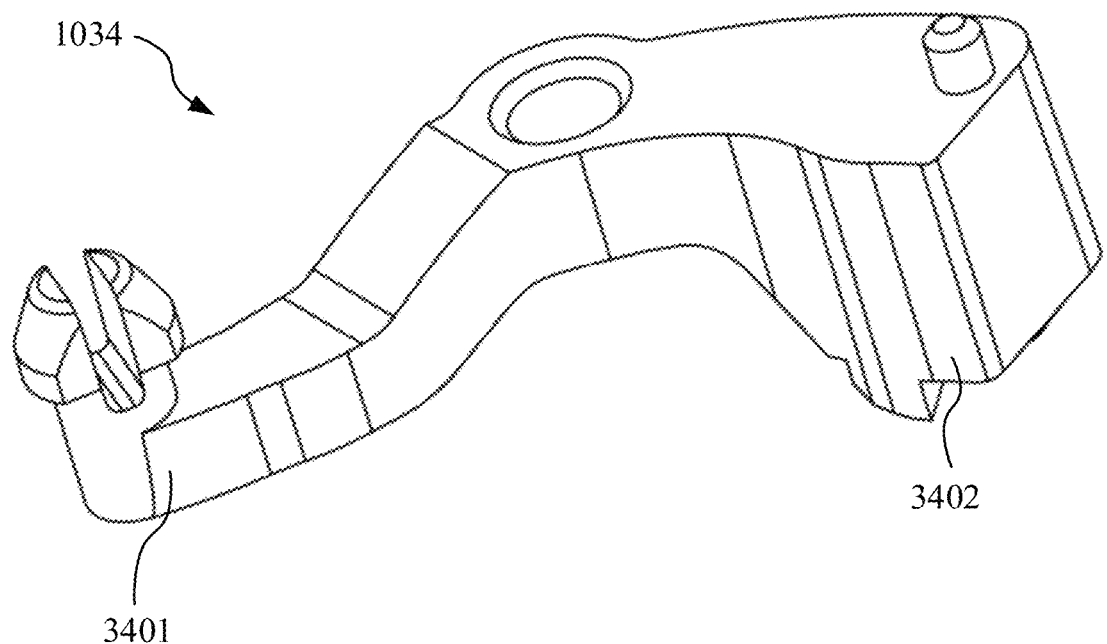
Figure 6:
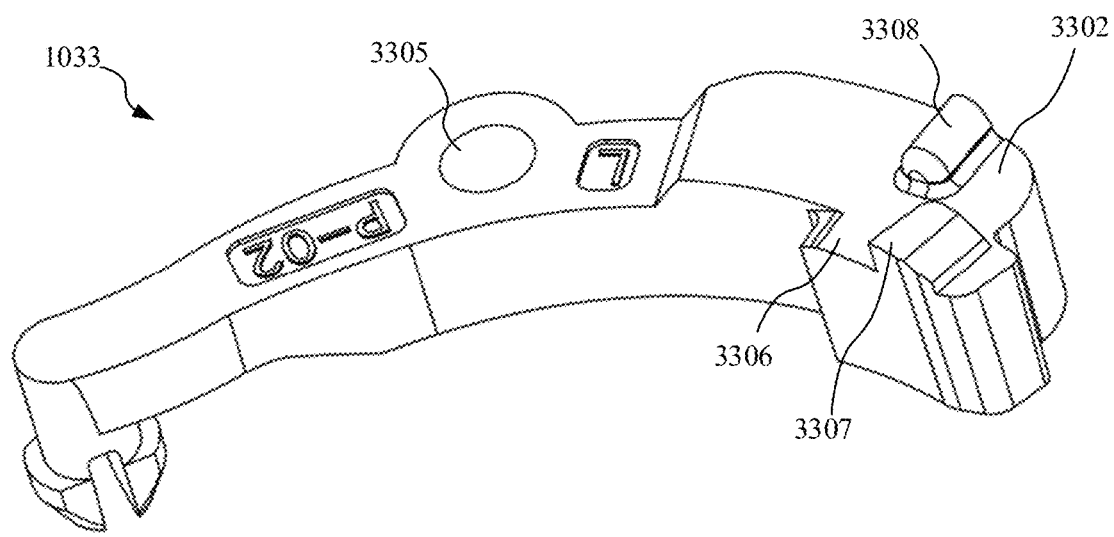
FIGS. 6 and 7 are schematic diagrams of the first arm and the second arm of FIG. 1 from another perspective, respectively.
Figure 7:
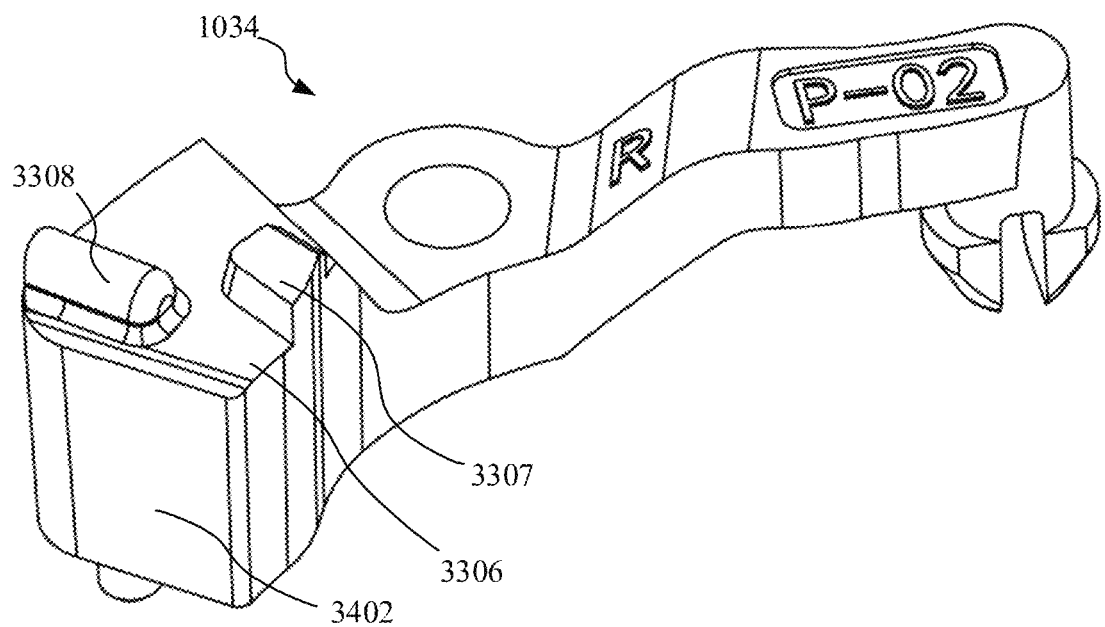
Figure 8:
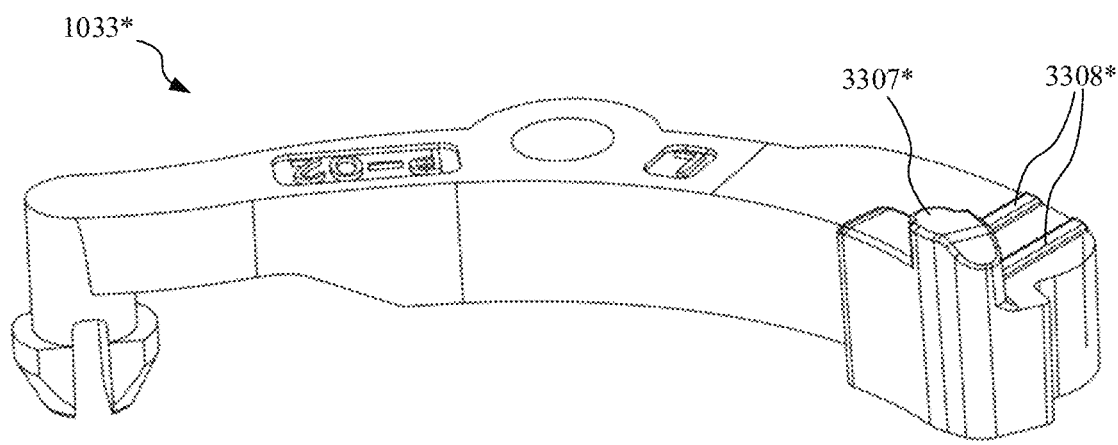
FIGS. 8 and 9 are schematic diagrams illustrating another embodiment of the first arm and the second arm of FIG. 1, respectively.
Figure 9:
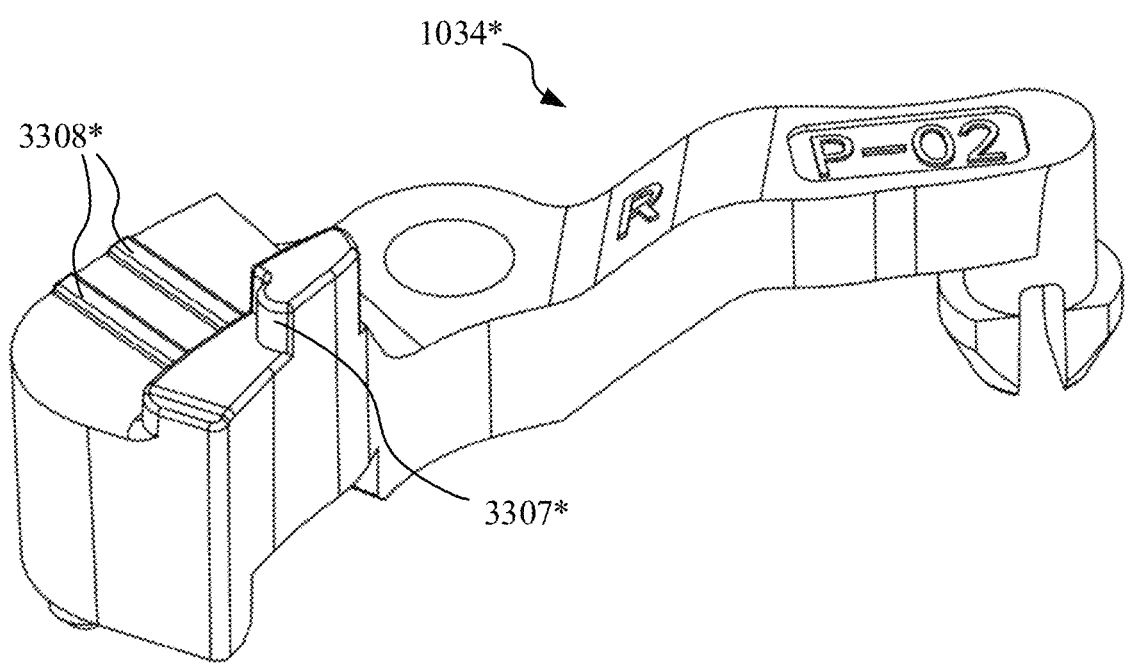
Figure 10:
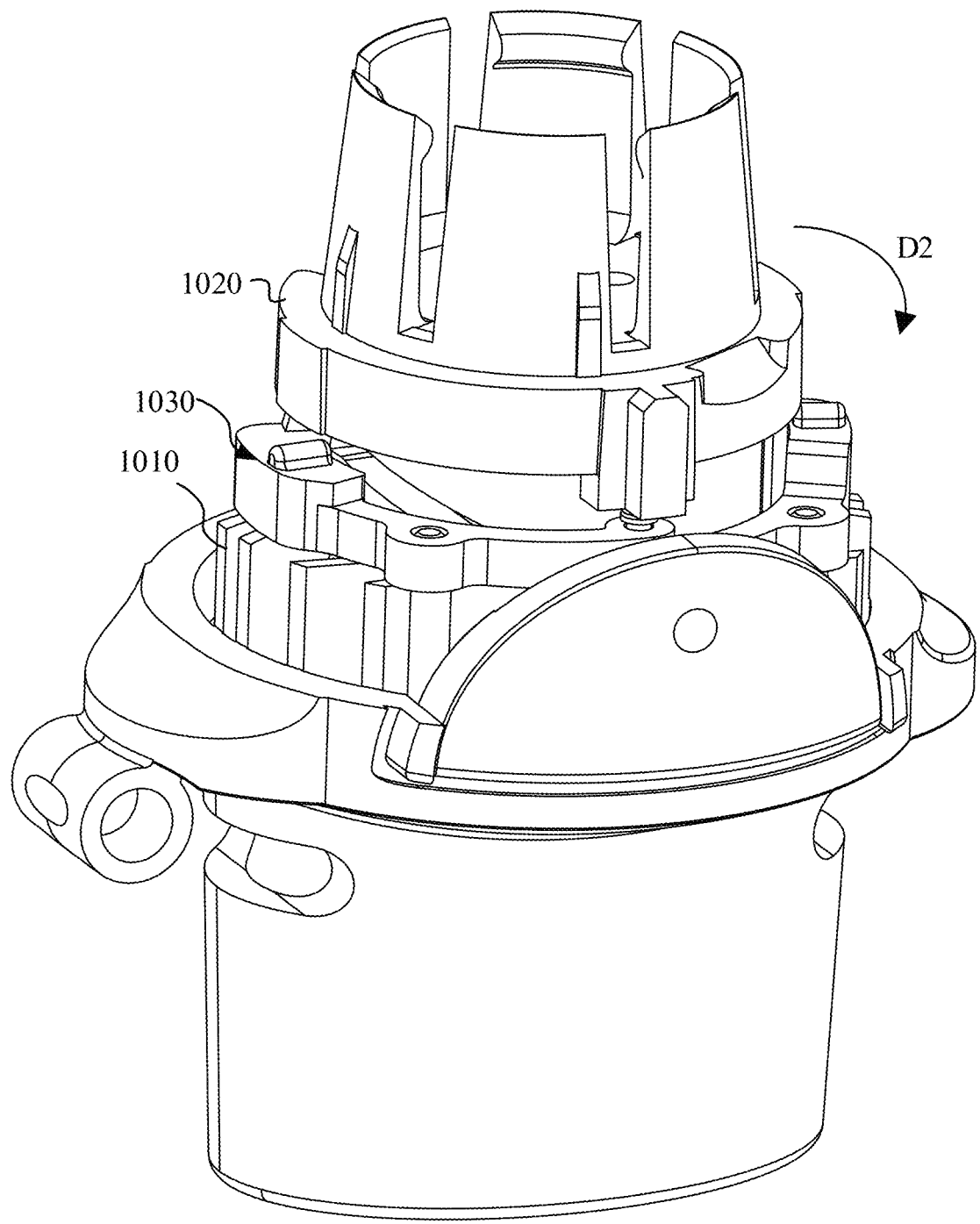
FIG. 10 is a schematic diagram illustrating a button assembly for an inhaler in a triggered position state according to an example embodiment.
Figure 11:
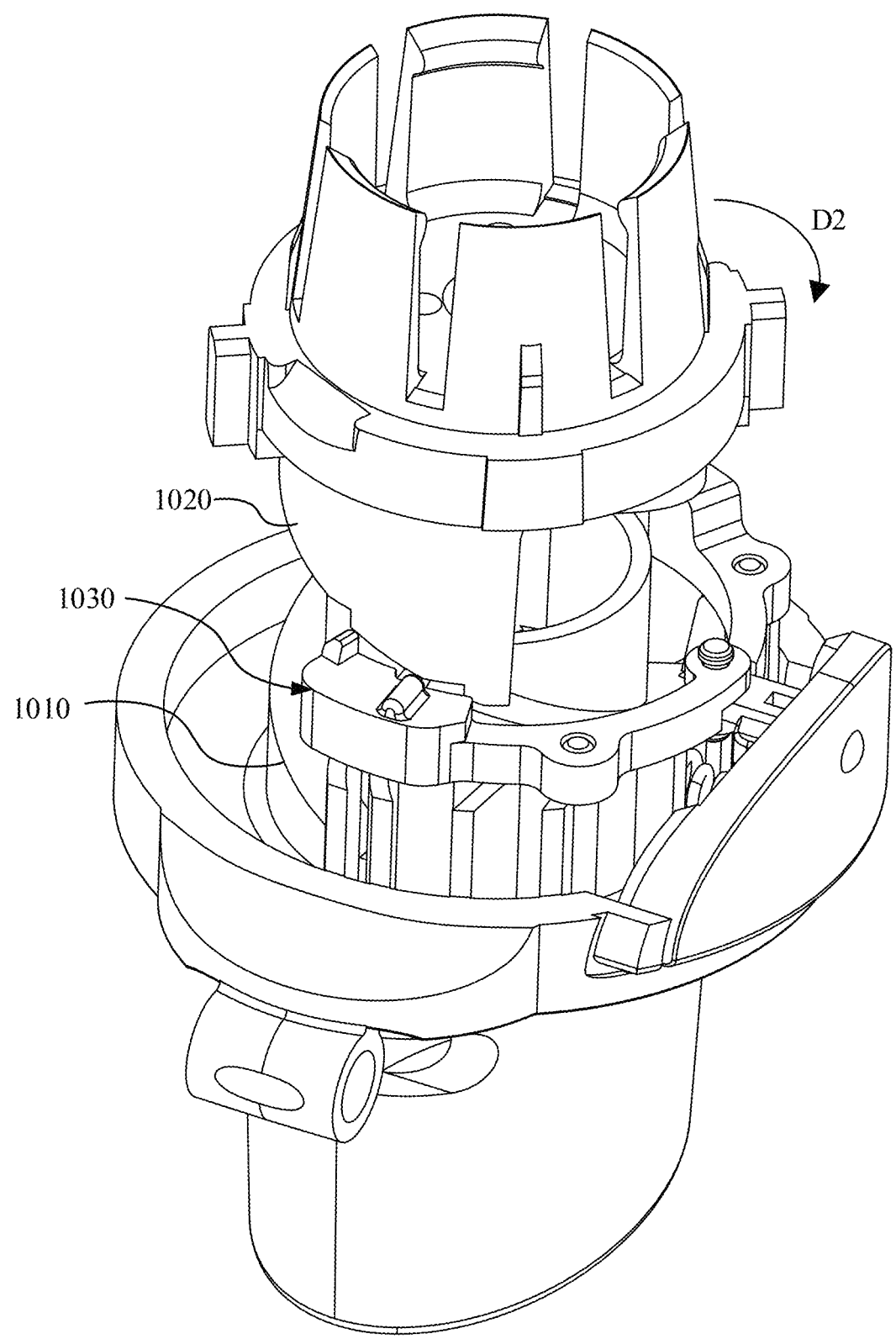
FIG. 11 is a schematic diagram illustrating a button assembly for an inhaler in an intermediate state according to an example embodiment.
Figure 12:
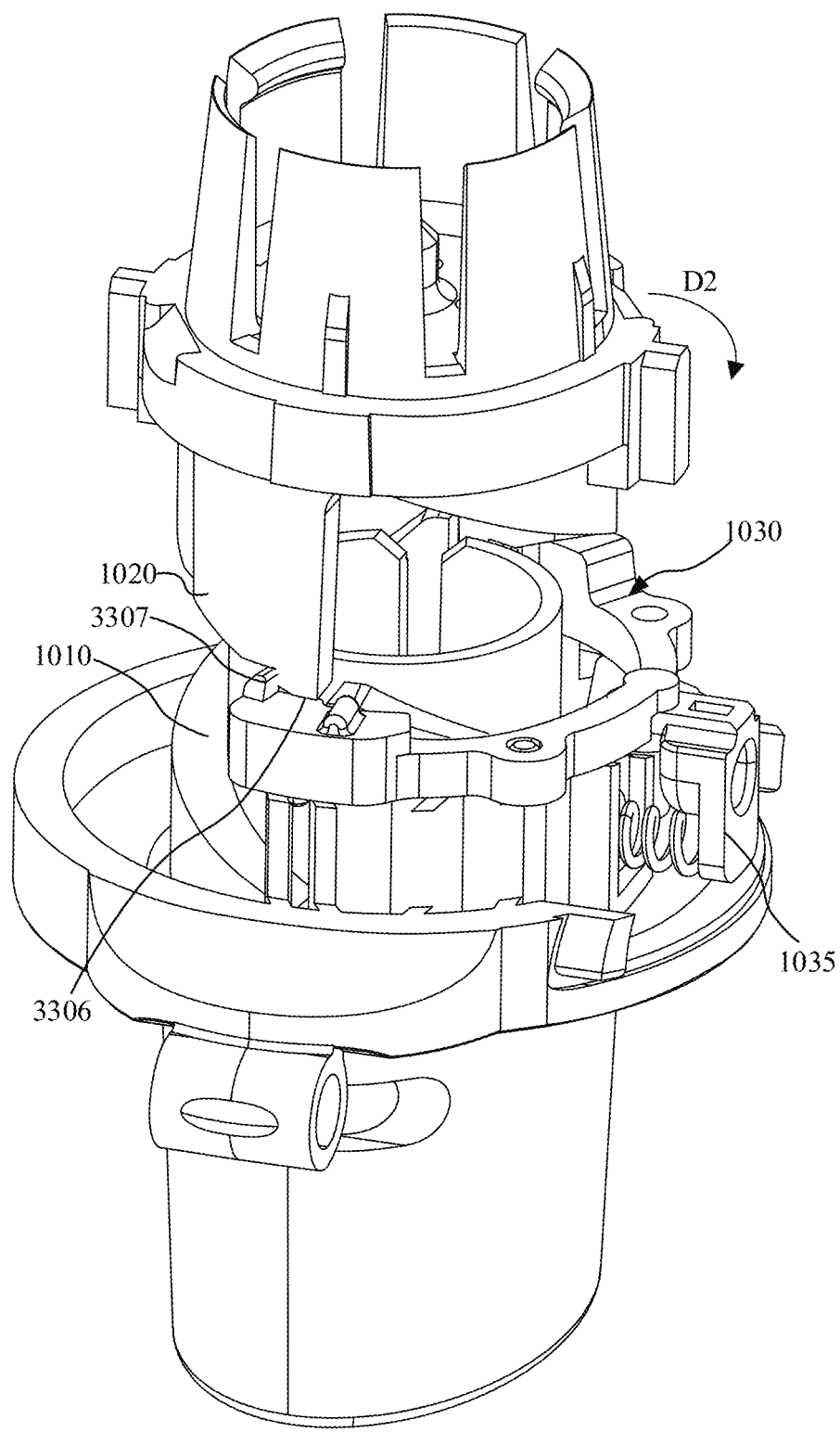
FIG. 12 is a schematic diagram illustrating a button assembly for an inhaler in a preloaded position state according to an example embodiment.

A trigger assembly according to an example embodiment is described below with reference to FIGS. 1-12. FIG. 1 is a schematic diagram illustrating a button assembly for an inhaler according to an example embodiment; FIG. 2 is a schematic diagram of a button body of the button assembly of FIG. 1; FIG. 3 is a schematic diagram of another embodiment of the button body of the button assembly of FIG. 2; FIGS. 4 and 5 are schematic diagrams of a first arm and a second arm of FIG. 1, respectively; FIGS. 6 and 7 are schematic diagrams of the first arm and the second arm of FIG. 1 from another perspective, respectively; FIGS. 8 and 9 are schematic diagrams illustrating another embodiment of the first arm and the second arm of FIG. 1, respectively; FIG. 10 is a schematic diagram illustrating a button assembly for an inhaler in a triggered position state according to an example embodiment; FIG. 11 is a schematic diagram illustrating a button assembly for an inhaler in an intermediate state according to an example embodiment; and FIG. 12 is a schematic diagram illustrating a button assembly for an inhaler in a preloaded position state according to an example embodiment.

Figure 17A:
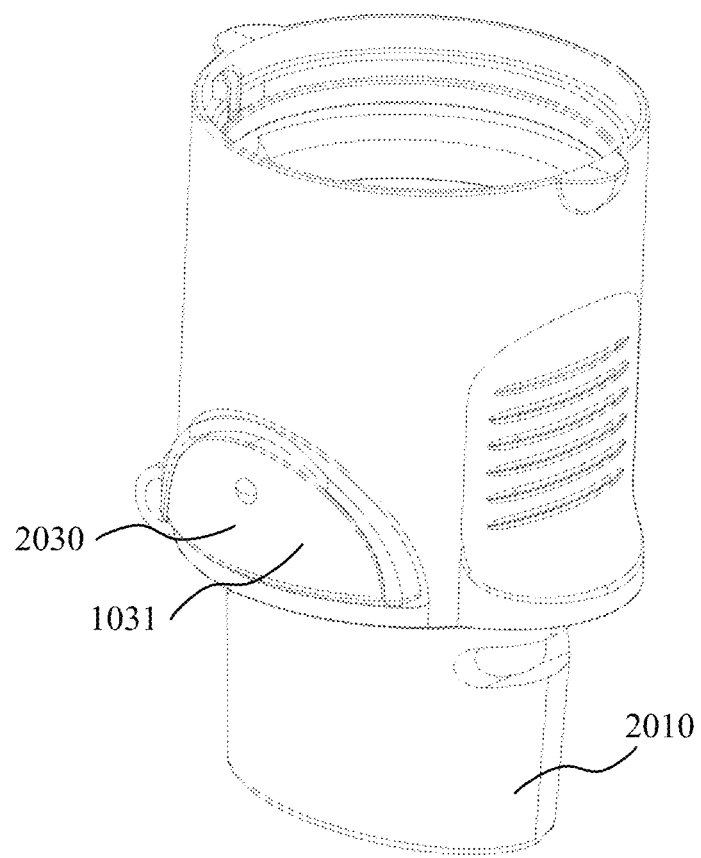
FIG. 17a and FIG. 17b are schematic diagrams illustrating a button of the inhaler of FIG. 13 unpressed and pressed respectively, wherein some components of the inhaler are omitted for simplicity of view.
Figure 17B:
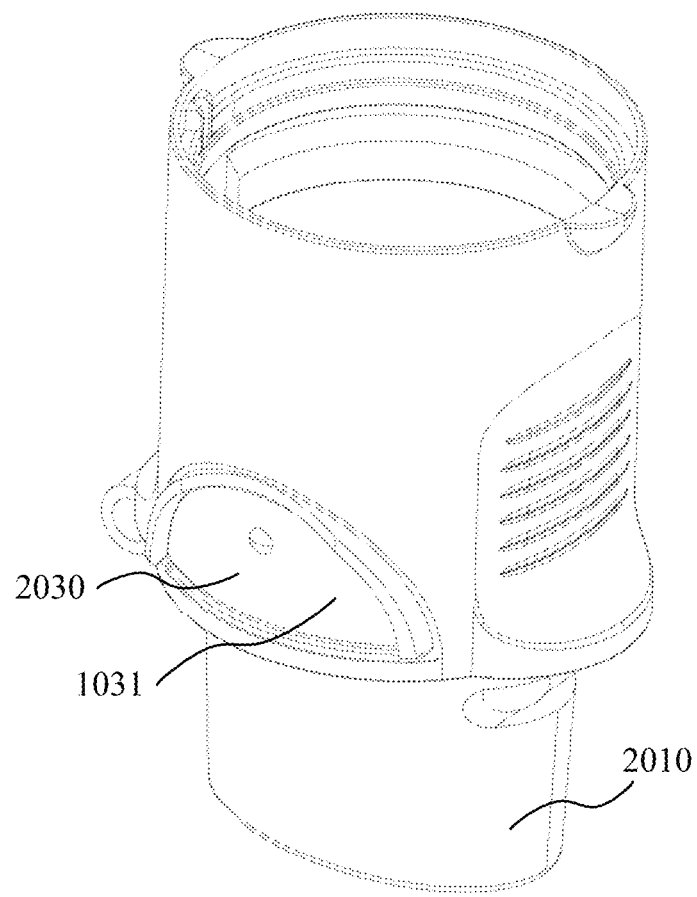

In the scope of the present disclosure, at least one arm of the button assembly 1030 has both a "closed" state and an "open" state. Referring to FIG. 17a and FIG. 17b, which are schematic diagrams illustrating the button 2030 of the inhaler 2000 of FIG. 3 unpressed and pressed respectively. The button 2030 also has corresponding position states when pressed and not pressed. It can be understood that in the pressed state, the button body 1031 of the button assembly 1030 can be recessed by an appropriate distance relative to the upper housing 2010 of the inhaler.

As shown in FIG. 1, at least one arm in the present disclosure may include only a first arm 1033, or only a second arm 1034, or include the first arm 1033 and the second arm 1034. In the following description, it will be appreciated that the first arm 1033 and the second arm 1034 can be replaced with an embodiment in which only the first arm 1033 or only the second arm 1034 is included, which is not limited herein.

As the inhaler is in a different position and moves accordingly, at least one arm in the present disclosure can also switch between respective movement states. If a distal end of the at least one arm opposite a proximal end is close to a housing of an inhaler, a button body 1031 stretches an elastic member 1032. If the distal end of the at least one arm is away from the housing of the inhaler, the button body 1031 presses the elastic member 1032.

In an example in which the at least one arm includes a first arm 1033 and a second arm 1034, when the inhaler is in the triggered position (initial position), the first arm and the second arm of the button assembly 1030 may be in an open state, and in this case, the respective distal ends of the first arm and the second arm are away from each other; and when the inhaler is in the preloaded position, the first arm and the second arm of the button assembly 1030 may be in a closed state, and in this case, the respective distal ends of the first arm and the second arm are close to each other (compared with the case in the open state).

According to the button assembly 1030 of the present disclosure, the at least one arm (e.g., the first arm 1033, the second arm 1034, or the first arm 1033 and the second arm 1034) and the elastic member 1032 are coupled to the button body 1031, such that when the at least one arm is in different states, the positions of the button body 1031 relative to the housing of the inhaler are different (due to the elastic deformation of the elastic member 1032), and the force feedbacks of the user pressing the button body 1031 are different, thereby providing the user with a clear feeling and feedback on the state of the inhaler, and contributing to improving the user experience and ease of use. Specifically, when the at least one arm is open (the triggered position), the at least one arm causes the button body 1031 to move inwards by means of coupling its proximal end to the button body 1031, the elastic member 1032 is in a compressed state, and at this point, it can be felt that the resistance is large and the travel generated when the button body 1031 is pressed is small. When the at least one arm is open (the preloaded position), the at least one arm is closed and forces the button body 1031 to move outwards by means of its proximal end, the elastic member 1032 is in a stretch state, and at this point, it can be felt that the resistance is small and the travel generated when the button body 1031 is pressed is large.

Furthermore, the design of the linkage between the button body 1031 and the at least one arm and the elastic member 1032 saves the interior space of the inhaler, making the overall structure of the inhaler more compact and durable. In addition, the elastic member 1032 is compressed and stretched during the use of the inhaler, such that a stress is evenly distributed, which prevents rapid aging caused by a unidirectional stress, thereby prolonging the service life of the inhaler.

Referring first to FIGS. 1-9, a button assembly 1030 for an inhaler includes: a button body 1031, an elastic member 1032, and a first arm 1033 and a second arm 1034.

As shown in FIG. 1, it can be seen that the elastic member 1032 has a first end 3201 and a second end 3202 opposite the first end 3201, wherein the first end 3201 is coupled to the button body 1031, and the second end 3202 is configured to be coupled to a housing of the inhaler. With further reference to FIGS. 4 and 5, the first arm 1033 has a first proximal end 3301 and a first distal end 3302, and the second arm 1034 has a second proximal end 3401 and a second distal end 3402, wherein the first proximal end 3301 of the first arm 1033 and the second proximal end 3401 of the second arm 1034 are coupled to the button body 1031.

In the case of the respective distal ends of the first arm 1033 and the second arm 1034 opposite the proximal ends being away from each other, the button body 1031 presses the elastic member 1032, and in the case of the respective distal ends of the first arm 1033 and the second arm 1034 being close to each other, the button body 1031 stretches the elastic member 1032.

In some embodiments, the first arm 1033, the second arm 1034 and the elastic member 1032 jointly act on the button body 1031 with a force between 5 N and 25 N. Herein a newton (N) is defined as 1 kg·m/s2. One newton (N) is, therefore, the force needed to accelerate one kilogram of mass at the rate of one metre per second squared in the direction of the applied force.

In some embodiments, the button assembly 1030 is configured to be pressed toward the housing of the inhaler when subjected to a pressing force ranging from 4 N to 20 N. In the present disclosure, a user actuates the button assembly 1030 by pressing a portion of the button assembly 1030 exposed outside the housing of the inhaler (the portion may be, for example, the button body 1031) to trigger the inhaler to perform a spraying operation. In the case of the user pressing the button body 1031, the first arm 1033, the second arm 1034 and the elastic member 1032 coupled to the button body 1031 have a blocking effect on the travel of the button body 1031, therefore, the pressing force (which may also be referred to as an activation force) required to press the button assembly 1030 needs to be adapted to the force with which the first arm 1033, the second arm 1034 and the elastic member 1032 jointly act on the button body 1031. For example, when the first arm 1033 and the second arm 1034 are in different (open or closed) states before and after drug administration, the button body 1031 and the elastic member 1032 are also in corresponding different states. The first arm 1033, the second arm 1034 and the elastic member 1032 jointly act on the button body 1031 with a resistance of between 4 N and 20 N, so the activation force required to be applied to the button body 1031 is between 4 N and 20 N.

In some embodiments, at least one of the first arm 1033 and the second arm 1034 have a first assembly portion 3303 at the proximal end thereof, and the button body 1031 has an assembly hole 3101 for fitting with the first assembly portion 3303. For example, referring to FIGS. 2 and 4, the first arm 1033 has a first assembly portion 3303 at the first proximal end 3301 thereof. When the first assembly portion 3303 is inserted into the assembly hole 3101 of the button body 1031, a precise mechanical fit is formed, which ensures the correct position of the first arm 1033 during assembly, and reduces the possibility of misalignment and loosening between parts.

With further reference to FIGS. 2-5, in some embodiments, the first assembly portion 3303 has a head 301 adapted to the shape of the assembly hole 3101 to allow the first assembly portion 3303 to be mounted into the assembly hole 3101 in a first direction D1. In some examples, for example as shown in FIG. 2, the assembly hole 3101 may have an elliptical shape or another suitable shape, and the contour shape of the outermost edge of the head 301 of the first assembly portion 3303 is adapted to the shape of the assembly hole 3101, such that the first arm 1033 can only be assembled in a specific direction (e.g., the first direction D1 as shown in FIG. 2). The head 301 and the assembly hole 3101 are shaped to further improve the accuracy and stability of assembly of the button assembly 1030.

Referring to FIG. 4, in some embodiments, the first assembly portion 3303 includes: a groove 302, the groove 302 being configured to extend toward a body portion of the first assembly portion 3033; and at least one first barb structure 303, wherein the first assembly portion 3303 is configured such that during mounting the first assembly portion 3303 into the assembly hole 3101, the groove 302 contracts to enable the at least one first barb structure 303 to pass through the assembly hole 3101, and the first barb structure 303 is configured to abut around the assembly hole 3101 when the first assembly portion 3303 is mounted in the assembly hole 3101.

The groove 302 is designed to allow the first assembly portion 3303 to contract when passing through the assembly hole 3101, such that the barb structure 303 passes smoothly through the hole, achieving quick and secure engagement. The first barb structure 303 is designed to contribute to preventing the mounted first assembly portion 3303 from being loosened/disengaged due to external forces, thereby improving the reliability of assembly, and avoiding the inconsistency of the pressing feeling about the button assembly 1030 or the position shift of the button caused by loosening.

In some examples, at least one first barb structure 303 may be symmetrically arranged on two sides of the groove 302, that is, two first barb structures 303 may be provided. In an embodiment according to the present disclosure, the first barb structure 303 can rotate in the assembly hole 3101 of the button body 1031, and the button body 1031 can move relative to the first arm 1033 and/or the second arm 1034 by means of the rotation of the first barb structure 303. It will be appreciated that the first barb structure 303 in the present disclosure may also be four first barb structures arranged symmetrically.

Figure 16:
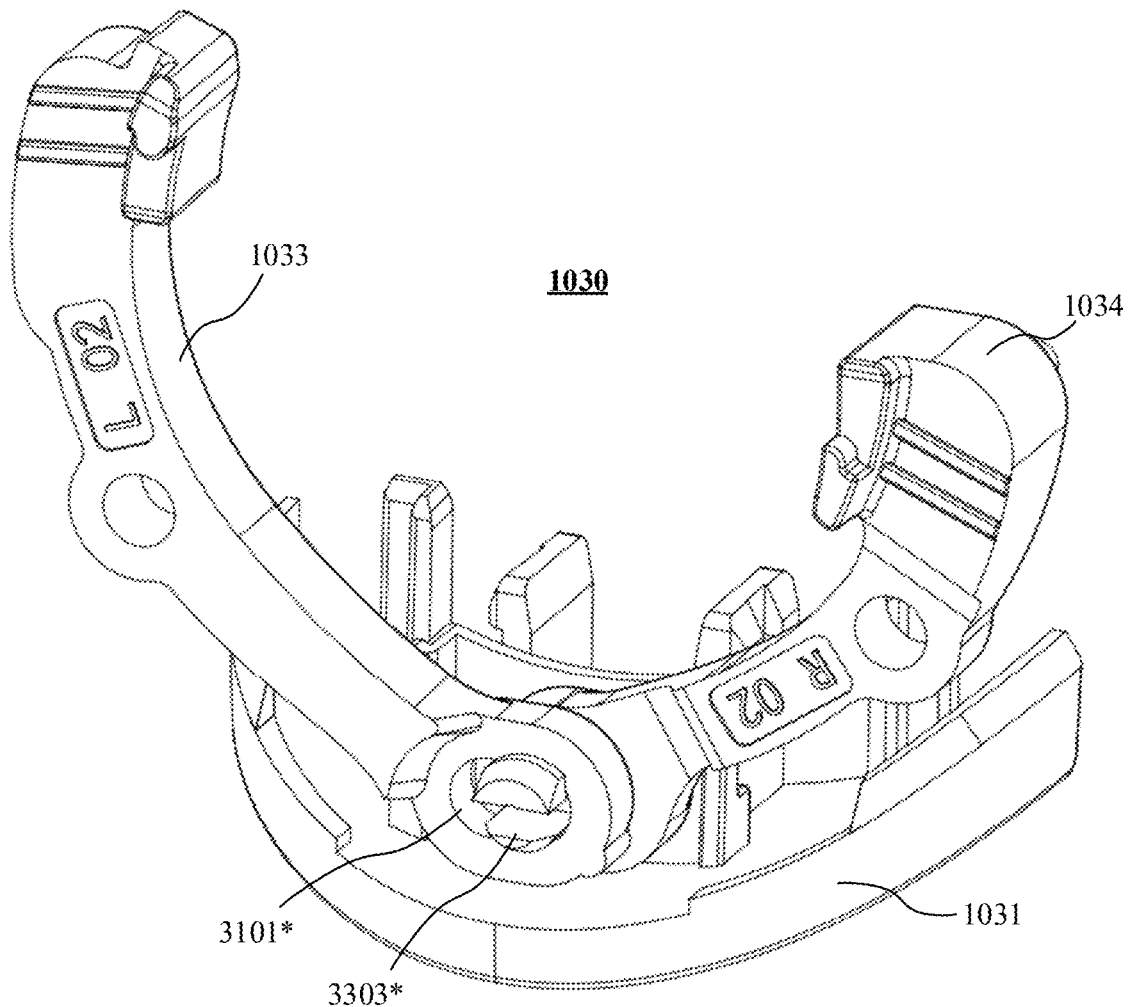
FIG. 16 is a schematic diagram of another embodiment of the button assembly of FIG. 1 from another perspective.

Referring to FIG. 16, which is a schematic diagram of another embodiment of the button assembly 1030 of FIG. 1 from another perspective, in some embodiments, at least one of the first arm 1033 and the second arm 1034 have a second assembly hole 3101* at the proximal end thereof, and the button body 1031 has a third assembly portion 3303* for fitting with the second assembly hole 3101*. In the above embodiment, the second assembly hole 3101* is provided on the button body 1031, so that when a user presses the button assembly 1030, the position of the pressing force applied can be more concentrated, so that the triggering of the button assembly 1030 can be more coherent without causing unexpected trigger inconsistence, and the pressing feel for users is more uniform, which improves the user experience. It will be appreciated that the third assembly portion 3303* can have a head, a groove, and a barb structure similar to the first assembly portion 3303, and its characteristics and functions are similar to those of the first assembly portion 3303, which will not be repeated here.

Referring to FIG. 2, in some embodiments, the button body 1031 has at least one insertion portion 3102 configured to be coupled to the housing of the inhaler, at least one second barb structure 3103 being provided on a head 301 of the at least one insertion portion 3102.

The at least one insertion portion 3102 is provided such that when the button assembly 1030 is mounted to the housing of the inhaler by means of the button body 1031, no additional tools or fasteners are required, and the second barb structure 3103 arranged on the head 301 of the insertion portion 3102 is automatically locked to an inner wall of the housing, thereby improving the assembly efficiency and reducing the production costs. Moreover, once the insertion is completed, during use, the second barb structure 3103 can be used to limit the return position of the button body 1031 by the second barb structure 3103 closely abutting against the interior of the housing, ensuring that the button assembly 1030 is securely fixed in the housing and is less likely to loosen.

In some examples, the insertion portion 3102 may have a plate-like structure, and the second barb structure 3103 may be arranged along a tail end of the plate-like structure. For example, as shown in FIG. 2, two second barb structures 3103 may be provided at the tail end of the insertion portion 3102. In addition, the at least one insertion portion 3102 may be arranged symmetrically with respect to the geometric center of the button body 1031, which contributes to improving the stability of mounting the button body 1031 to the housing of the inhaler.

It can be appreciated that, as shown in FIGS. 5 and 7, the second arm 1034 of the button assembly 1030 may have an assembly portion and a head on the assembly portion that are similar to those of the first arm 1033, and that have the same features and functions as the first assembly portion 3303 and the head 301 of the first arm 1033, which will not be repeated here.

With continued reference to FIG. 2, in some embodiments, the button body 1031 has a second assembly portion 3104, the first end 3201 of the elastic member 1032 is sleeved on the second assembly portion 3104, and the second end 3202 of the elastic member 1032 is connected to the housing of the inhaler. The elastic member 1032 is sleeved on the second assembly portion 3104, which makes the process of assembly simple and quick, and the mounting of the elastic member 1032 can be completed without complicated tools, thereby reducing the manufacturing costs. In addition, two ends of the elastic member 1032 are connected to the button body 1031 and the housing of the inhaler, respectively, which facilitates the axial positioning of the elastic member 1032 and improves the assembly stability of the assembly.

Referring further to FIG. 3, in the embodiment of the button body 1031 shown in FIG. 3, a guide portion 3105 is provided on the button body 1031. The guide portion 3105 may fit with a corresponding guide feature of the inhaler to improve the accuracy of mounting of the button body 1031, and in the case of the button body 1031 being pressed, the arrangement of the guide portion 3105 contributes to maintaining the direction of a pressing force, to avoid the instability of the button body 1031, thereby improving the user experience. In some embodiments, two guide portions 3105 may be provided, for example, as shown in FIG. 3, the button body 1031 may have two guide portions 3105 that are symmetrical with respect to the central axis of the button body 1031. In some examples, the guide portion 3105 have a cross section of an "L" shape to improve the assembly efficiency and positioning accuracy of the guide portion 3105 with a corresponding guide feature of the inhaler.

In some examples, the elastic member 1032 may be centrally arranged on the button body 1031, which facilitates the uniform stress on the button body 1031 and improves the overall pressing feeling for the button assembly 1030.

In some embodiments, the elastic member 1032 is a spring, the second assembly portion 3104 is shaped to be adapted to an inner diameter of the spring 1032, and the second assembly portion 3104 is in interference fit with the spring 1032. In the example shown in FIGS. 1 and 2, the shape of the second assembly portion 3104 is adapted to the elastic member 1032, for example, the second assembly portion 3104 may be cross-shaped, the cross-shaped contour is adapted to the inner diameter of the elastic member 1032, and the second assembly portion 3104 may be in interference fit with the elastic member 1032 by means of its cross-shaped contour or any other suitable shape.

The shape of the second assembly portion 3104 is adapted to the inner diameter of the elastic member 1032, which facilitates the radial positioning of the elastic member 1032 and prevents the elastic member 1032 coupled to the button body from position change or shift during pressing, further improving the assembly stability of the assembly.

In some embodiments, the pressing force is related to the elastic force of the elastic member 1032 acting on the button body 1031. For example, a magnitude of the elastic force of the elastic member 1032 acting on the button body 1031 is between 2 N and 8 N.

In some examples, the inhaler further includes: a first component 1010 and a second component 1020, wherein the first component 1010 and the second component 1020 are configured such that when the second component 1020 rotates relative to the first component 1010 in a second direction, the second component 1020 can move away from the first component 1010 to the preloaded position, and wherein the first arm 1033 and the second arm 1034 are arranged partially around the first component 1010 and/or the second component 1020, and when the second component 1020 moves toward the preloaded position, the first arm 1033 and the second arm 1034 slide relative to an outer peripheral surface of the second component 1020 to allow the respective distal ends (3302 and 3402) of the arm (the first arm 1033 and the second arm 1034) to move close to each other.

It can be seen that the second component 1020 in FIG. 10 is in the triggered position (also the initial position), in this case, the first arm 1033 and the second arm 1034 of the button assembly 1030 are in the open state, and the button body 1031 presses the elastic member 1032. The second component 1020 in FIG. 12 is in the preloaded position, in this case, the first arm 1033 and the second arm 1034 of the button assembly 1030 are in the closed state, and the button body 1031 stretches the elastic member 1032. The second component 1020 in FIG. 11 is in an intermediate state between the triggered position and the preloaded position. When the second component 1020 rotates relative to the first component 1010 in the second direction, at least one arm of the button assembly 1030 (e.g., the first arm 1033 and/or the second arm 1034) always surrounds the first component 1010 and/or the second component 1020, therefore, the first component 1010 and/or the second component 1020 can be prevented from being undesirably disengaged from the at least one arm, so as to prevent accidental spraying by the inhaler. In some examples, the second component 1020 is configured as a delivery tube holder of the inhaler (also referred to as a tube rack), and at least one arm of the button assembly 1030 can always hold the tube rack to prevent undesired accidental spraying during rotation.

In an example, in the preloaded position, a liquid drug may be pumped from a reservoir into a pumping chamber located at the first component 1010 or the second component 1020; and in the triggered position, the liquid drug can be sprayed from the pumping chamber outwards through a nozzle, and accordingly, after the spraying is completed, the second component 1020 in the triggered position is in an initial position of the next cycle of action and can thus move to the preloaded position again.

The button assembly 1030 according to the present disclosure can realize that before and after the inhaler pumps the liquid drug to the pumping chamber, i.e., when the first arm 1033 and the second arm 1034 are in different states, the positions of the button body 1031 relative to the housing of the inhaler are different (due to the elastic deformation of the elastic member 1032), and the force feedbacks of the user pressing the button body 1031 are different, thereby providing the user with a clear feeling and feedback on the state of the inhaler, and contributing to improving the user experience and ease of use.

The first component 1010 and the second component 1020 are configured such that the second component 1020 can move away from the first component 1010 to the preloaded position when rotating relative to the first component 1010 in the second direction D2. For example, with reference to FIGS. 10-12, starting from the position as shown in FIG. 10, the second component 1020 rotates relative to the first component 1010 in a clockwise direction in FIG. 10, and as shown in FIG. 10, as the second component 1020 rotates, the second component 1020 gradually moves away from the first component 1010; and as the second component 1020 further rotates in the clockwise direction, the second component 1020 moves to the preloaded position as shown in FIG. 12. In an example, the rotational movement between the first component 1010 and the second component 1020 may also be converted to a relative translation therebetween by means of a gear and rack mechanism or a screw mechanism.

As shown in FIGS. 10 to 12, as an alternative form, the first arm, the second arm and the elastic member 1032 may also be coupled to the button body 1031 by means of a button connector 1035 (only indicated in FIG. 12 for simplicity of view). For example, the first arm, the second arm and the elastic member 1032 are first connected to the button connector 1035, and the button connector 1035 is then connected to the button body 1031. It will be appreciated that the button assembly 1030 in FIGS. 10 to 12 may also be replaced with the button assembly 1030 shown in FIG. 1, has features and functions similar to those of the button assembly 1030 according to the present disclosure, which will not be repeated here.

In some examples, the first arm 1033 and the second arm 1034 of the button assembly 1030 may be arranged partially around the first component 1010 and/or the second component 1020. For example, the first arm 1033 and the second arm 1034 of the button assembly 1030 may be connected to the first component 1010, and arranged partially around an outer periphery of the first component 1010. Alternatively, the first arm 1033 and the second arm 1034 of the button assembly 1030 may be connected to the second component 1020 and arranged partially around an outer periphery of the second component 1020. Alternatively, the first arm 1033 and the second arm 1034 of the button assembly 1030 may be connected to and arranged partially around both the first component 1010 and the second component 1020.

In some embodiments, as shown in FIGS. 4-7, at least one of the first arm 1033 and the second arm 1034 includes a connecting portion 3305. The connecting portion 3305 is pivotally connected to the first component 1010 and/or the second component 1020, such that when the button body 1031 is pressed, the respective first arm 1033 and/or second arm 1034 pivot around the connecting portion 3305.

For example, as shown in FIGS. 10-11, the connecting portion 3305 can be pivotally connected to a shaft of the first component 1010, such that when the user presses the button assembly 1030 (e.g., presses the button body 1031 or the button connector), the first proximal end 3301 of the first arm 1033 moves radially inwards (toward the first component 1010), causing the curved first arm to rotate about its own connecting portion 3305, whereby the first distal end 3302 of the first arm 1033 will move radially outwards (away from the first component 1010). It will be appreciated that the second arm 1034 may likewise have a corresponding connecting portion 3305 whose features and functions are similar to those of the connecting portion 3305 of the first arm, which will not be repeated here. That is, when the user presses the button, the distal end of the first arm 1033 and the distal end of the second arm 1034 will be away from each other.

In some embodiments, the distal end of the first arm 1033 and/or the second arm 1034 includes a bearing portion 3306 extending radially inwards from a main body thereof. The bearing portion 3306 is configured to abut against the second component 1020 when the first arm 1033 and/or the second arm 1034 slide relative to the outer peripheral surface of the second component 1020.

For example, a main body of the first arm 1033 and/or the second arm 1034 may have a substantially annular shape to enable an inner periphery thereof to substantially surround the first component 1010 or the second component 1020 having a substantially cylindrical outer surface. The bearing portion 3306 of the first arm 1033 and/or the second arm 1034 extends radially inwards from the annular main body. As shown in FIG. 8, the first distal end 3302 of the first arm 1033 has a bearing portion 3306. It will be appreciated that the second arm 1034 may also have a corresponding bearing portion 3306, which will not be repeated here.

As can be seen from FIGS. 10-12, during the rotation of the second component 1020 relative to the first component 1010, since the first arm 1033 and/or the second arm 1034 surrounds the periphery of the first component 1010 and/or the second component 1020, thus not interfering with the rotation of the second component 1020. On the contrary, as the second component 1020 rotates, the first arm 1033 and/or the second arm 1034 will slide relative to the outer peripheral surface of the second component 1020. When the second component 1020 is moved to the preloaded position as shown in FIG. 12, the bearing portion 3306, which extends radially inwards, of the first arm 1033 and/or the second arm 1034 can abut against the second component 1020 due to being radially closer to the inner side relative to the main body, thereby preventing the second component 1020 from leaving the preloaded position.

For example, an upper surface of the bearing portion 3306 in FIG. 12 abuts against a lower surface of a portion of the second component 1020, so as to prevent further downward movement of the second component 1020 away from the preloaded position.

In some embodiments, the first arm 1033 and/or the second arm 1034 can be configured such that when the second component 1020 is disengaged from the first component 1010, the second component 1020 can just abut against the bearing portion 3306 of the first arm 1033 and/or of the second arm 1034. For example, the first arm 1033 and/or the second arm 1034 may be constructed by setting the size of the main body of the first arm 1033 and/or the second arm 1034 (or the position of the bearing portion 3306 of the first arm 1033 and/or the second arm 1034). In an example, the first arm 1033 and/or the second arm 1034 may be connected to the first component 1010, and the bearing portion 3306 of the first arm 1033 and/or the second arm 1034 may be positioned at a position where the second component 1020 is just disengaged from the first component 1010. Thereby, when the second component 1020 is disengaged from the first component 1010, the bearing portion 3306 smoothly abuts against the second component 1020, thereby achieving a smooth transition of the second component 1020 from the intermediate state to the preloaded state, without causing a small amount of liquid spray caused by a non-smooth transition.

In some embodiments, when the second component 1020 moves to the preloaded position, the bearing portion 3306 is configured to be disengaged from the second component 1020 to release the second component 1020 when the button body 1031 is pressed. For example, the first arm 1033 and/or the second arm 1034 may be constructed by setting the size of the bearing portion 3306 of the first arm 1033 and/or the second arm 1034. In an example, with continued reference to FIGS. 1-6, the distance by which the bearing portion 3306 extends inwards does not need to be very large, as long as the requirement of abutment against the second component 1020 can be met. In this way, when it is necessary for the second component 1020 to switch from the preloaded position to the triggered position, the second component 1020 can be released only by slightly moving the position of the bearing portion 3306 (e.g., slightly moving the bearing portion 104 radially outwards in FIG. 6).

In some embodiments, the button assembly 1030 further includes a further elastic member 1036. The further elastic member 1036 is configured to store energy when the second component 1020 moves away from the first component 1010, and when the bearing portion 3306 is disengaged from the second component 1020, the second component 1020 moves toward the first component 1010 to the triggered position under the action of the further elastic member 1036.

The further elastic member 1036 is configured to store energy when the second component 1020 moves away from the first component 1010. For example, the further elastic member 1036 may be a spring or another elastic member, as long as energy can be stored by means of elastic deformation. In an example, the further elastic member 1036 (e.g., a spring) may be arranged on a side of the second component 1020 close to the first component 1010, and is subjected to tensile deformation to store energy when the second component 1020 moves away from the first component 1010, and the second component 1020 can be pushed to the triggered position by means of a pull force when the further elastic member 1036 restores. In some embodiments, the further elastic member 1036 (e.g., a spring) may be arranged on a side of the second component 1020 away from the first component 1010, and is subjected to compression deformation to store energy when the second component 1020 moves away from the first component 1010, and the second component 1020 can be pushed to the triggered position by means of a push force when the further elastic member 1036 restores.

Referring back to FIGS. 6-9, the first distal end 3302 and the second distal end 3402 may each include a limiting protrusion 3307. The limiting protrusion 3307 is arranged adjacent to the bearing portion 3306 and protrudes from a bearing surface of the bearing portion 3306. The limiting protrusion 3307 is used to prevent the second component 1020 from rotating in the second direction D2 when the bearing portion 3306 abuts against the second component 1020.

In some examples, when the second component 1020 is in the preloaded position, the bearing portion 3306 abuts against the second component 1020, and the limiting protrusion 3307 prevents the second component 1020 from rotating in the second direction D2, such that unexpected rotation in the second direction D2 between the second component 1020 and the first component 1010 can be prevented. In some embodiments, a limiting step is provided at a tail end of the second component 1020, and the limiting protrusion 3307 prevents the second component 1020 from rotating in the second direction D2 by abutting against the limiting step. In some embodiments, when the bearing portion 3306 abuts against the second component 1020, the limiting protrusion 3307 tangentially contacts the second component 1020 to prevent the second component 1020 from rotating in the second direction D2. The above-mentioned tangential contact can be achieved by configuring one of the limiting protrusion 3307* and the second component 1020 to have an arc shape. For example, in the embodiment shown in FIGS. 8 and 9, a surface of the limiting protrusion 3307* for preventing the second component 1020 from rotating in the second direction D2 has an arc shape. In some examples, it is also possible that a surface of the second component 1020 in contact with the limiting protrusion 3307* has an arc shape, and the corresponding surface of the limiting protrusion 3307* may be flat, for example. When the inhaler is in the preloaded position, the button assembly 1030 is pressed by the user to cause the button body 1031 to push the first arm 1033 and the second arm 1034 and will be obstructed by a frictional force between the first arm 1033 and/or the second arm 1034 and the second component 1020 (e.g., a frictional force at the bearing portion 3306 and the arc-shaped surface of the limiting protrusion 3307), so the magnitude of this frictional force can affect the activation force required to be applied to the button body 1031. By means of the tangential contact between the limiting protrusion 3307* and the second component 1020 (for example, by configuring the surface of the limiting protrusion 3307* for preventing the second component 1020 from rotating in the second direction D2 to have an arc shape), the magnitude of the above-mentioned frictional force can be controlled within a desired range, thereby improving the pressing feeling of the user. For example, compared with the case where the surface is flat, the arc-shaped surface can appropriately reduce the above-mentioned frictional force, thereby achieving a smoother pressing operation.

In some embodiments, the pressing force is related to the frictional force between each of the at least one arm and the second component. In some examples, the magnitude of the frictional force between the first arm 1033 or the second arm 1034 and the second component 1020 is between 1 N and 6 N.

Figure 13:
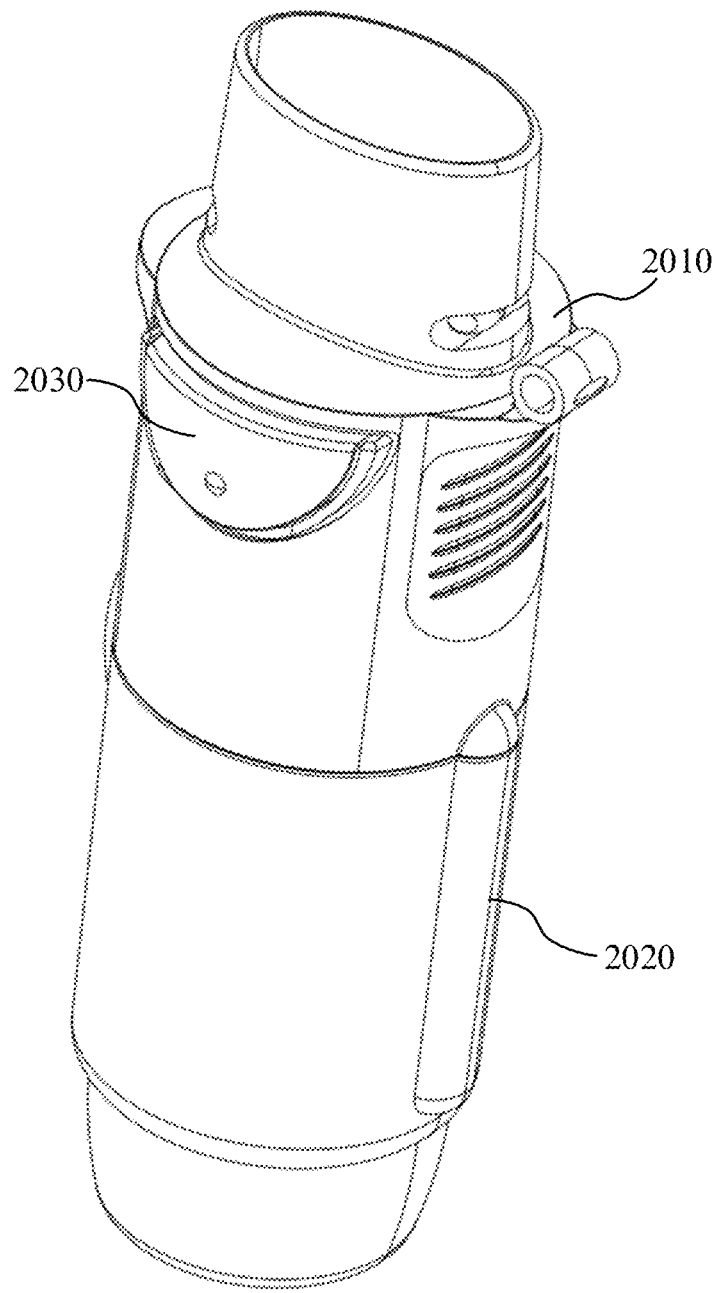
FIG. 13 is a perspective view illustrating an inhaler according to an example embodiment.
Figure 14:
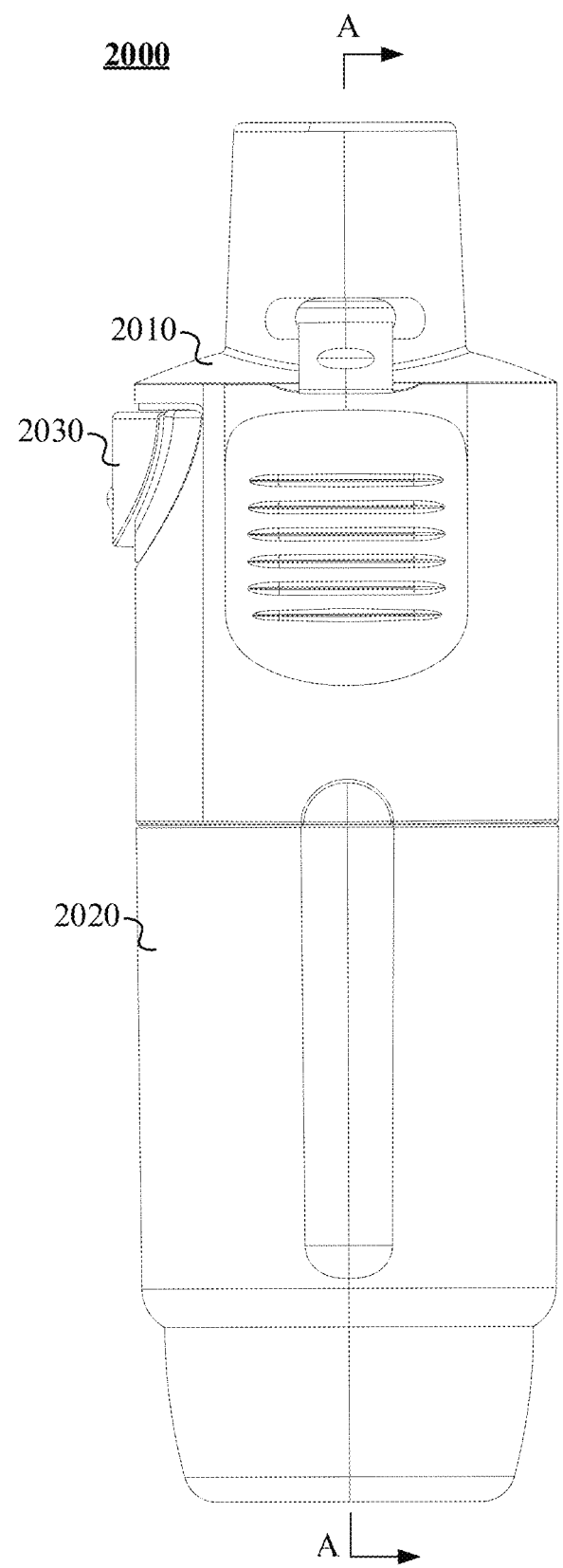
FIG. 14 is a side view illustrating an inhaler according to an example embodiment.
Figure 15:
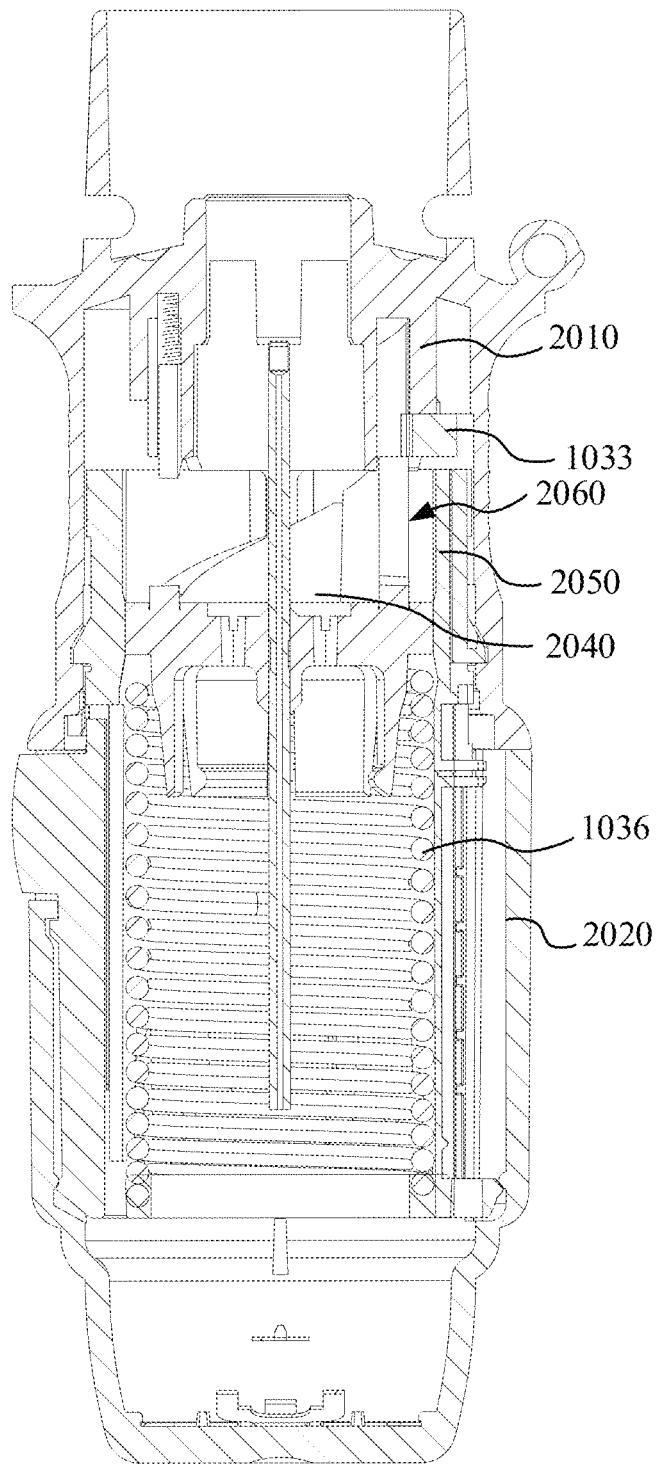
FIG. 15 is a cross-sectional view of the inhaler of FIG. 14 along section A-A.

According to a second aspect of the present disclosure, an inhaler is provided. The inhaler of the present disclosure is described below with reference to FIGS. 13 to 15. FIG. 13 is a perspective view illustrating an inhaler according to an example embodiment; FIG. 14 is a side view illustrating an inhaler according to an example embodiment; and FIG. 15 is a cross-sectional view of the inhaler of FIG. 14 along section A-A.

An inhaler 2000 includes a spray assembly and a button assembly 1030 according to the present disclosure, the button assembly 1030 being configured to be pressed to actuate the spray assembly to spray a liquid. A spray assembly 2060 can be mounted into the inhaler 2000 and may be linked with the button assembly 1030 of the inhaler, the spray assembly being configured to deliver the nebulized liquid to be sprayed into a corresponding chamber.

As shown in FIGS. 13 and 14, the inhaler 2000 may include an upper housing 2010, a lower housing 2020, and a button 2030 arranged on a portion of the upper housing. In addition, as shown in FIG. 15, the inhaler 2000 may further include a delivery tube holder 2040 and a rotating housing 2050 arranged inside the lower housing 2020.

In some embodiments, the first component 1010 may be configured as the upper housing 2010 of the inhaler 2000, the second component 1020 is configured as the delivery tube holder 2040 of the inhaler 2000, and the delivery tube holder 2040 is configured to be able to rotate as the lower housing 2020 of the inhaler 2000 rotates.

For example, the upper housing 2010 and the lower housing 2020 is rotatable relative to each other, and the delivery tube holder 2040 is coupled to the lower housing 2020. By rotating the lower housing 2020 relative to the upper housing 2010, the delivery tube holder 2040 can be rotated relative to the upper housing 2010. In other words, by rotating the lower housing 2020 relative to the upper housing 2010, the second component 1020 of a trigger assembly 1000 arranged in the inhaler 2000 can rotate relative to the first component 1010, and the second component 1020 moves away from the first component 1010 to the preloaded position. In this process, part of the liquid stored in a tank of the inhaler 2000 may be pumped, for example, into a pumping chamber of the inhaler 2000 for nebulization and spraying.

In some embodiments, the inhaler 2000 includes a rotating housing 2050, wherein the rotating housing 2050 is configured to accommodate at least a portion of the spray assembly 2060, and at least one of the first arm 1033 and the second arm 1034 has, at the distal end thereof, a fitting portion fitting with the rotating housing. In some examples, the fitting portion may be a protrusion arranged on the first arm and/or second arm (a fitting portion 3308 as shown in FIGS. 6 and 7) or a plurality of elongated prisms (a fitting portion 3308* as shown in FIGS. 8 and 9).

In some examples, the rotating housing 2050 is located inside the lower housing 2020 and is arranged outside the delivery tube holder 2040. The rotating housing 2050 can transmit the rotation of the lower housing 2020 to the delivery tube holder 2040. In other words, when the rotating housing 2050 rotates, the delivery tube holder 2040 also rotates along with the rotating housing. In addition, when the delivery tube holder 2040 is released and moves toward the upper housing 2010, the rotating housing 2050 does not move upwards along with the delivery tube holder 2040.

In the claims, the word "comprising" does not exclude other elements or steps not listed, the indefinite article "a" or "an" does not exclude plural, the term "a plurality of" means two or more, and the term "based on" should be interpreted as "at least partially based on". The mere fact that certain measures are recited in mutually different dependent claims does not indicate that a combination of these measures cannot be used to get benefit.

LIST OF REFERENCE SIGNS

- first component 1010; second component 1020;
- button assembly 1030;
- button body 1031, assembly hole 3101, second assembly hole 3101*, insertion portion 3102, second barb structure 3103, second assembly portion 3104, guide portion 3105;
- elastic member 1032, first end 3201, second end 3202;
- first arm 1033, first arm 1033*, first proximal end 3301 of first arm, first distal end 3302 of first arm, first assembly portion 3303, third assembly portion 3303*, connecting portion 3305, bearing portion 3306, limiting protrusion 3307, 3307*, fitting portion 3308, 3308*;
- head 301, groove 302, first barb structure 303;
- second arm 1034, 1034*, second proximal end 3401 of second arm, second distal end 3402 of second arm;
- button connector 1035;
- further elastic member 1036;
- inhaler 2000;
- upper housing 2010, lower housing 2020, button 2030, delivery tube holder 2040;
- rotating housing 2050;
- spray assembly 2060;
- first direction D1, second direction D2.

Although the detailed description makes reference to specific embodiments, the invention shall be defined solely by the appended claims and the equivalents thereof.

What is claimed is:

1. A button assembly for an inhaler, the button assembly comprising:

a button body;

an elastic member having a first end and a second end opposite the first end, wherein the first end is coupled to the button body, and the second end is used to be coupled to a housing of the inhaler; and at least one arm having a proximal end coupled to the button body, wherein when a distal end of the at least one arm opposite the proximal end is close to the housing of the inhaler, the button body stretches the elastic member.

2. The button assembly according to claim 1, wherein when the distal end of the at least one arm is away from the housing of the inhaler, the button body presses the elastic member.

3. The button assembly according to claim 1, wherein the button assembly is configured to be pressed toward the housing of the inhaler when subjected to a pressing force ranging from 4 N to 20 N.

4. The button assembly according to claim 1, wherein the at least one arm has a first assembly portion at the proximal end, and the button body has an assembly hole for fitting with the first assembly portion.

5. The button assembly according to claim 4, wherein the first assembly portion has a head adapted to the shape of the assembly hole to allow the first assembly portion to be mounted into the assembly hole in a first direction.

6. The button assembly according to claim 4, wherein the first assembly portion comprises:

a groove configured to extend toward a body portion of the first assembly portion; and at least one first barb structure, wherein the first assembly portion is configured such that during mounting the first assembly portion into the assembly hole, the groove contracts to enable the at least one first barb structure to pass through the assembly hole, and the first barb structure is configured to abut around the assembly hole when the first assembly portion is mounted in the assembly hole.

7. The button assembly according to claim 1, wherein the button body has at least one insertion portion configured to be coupled to the housing of the inhaler, at least one second barb structure being provided on a head of the at least one insertion portion.

8. The button assembly according to claim 1, wherein the button body has a second assembly portion, the first end of the elastic member is sleeved on the second assembly portion, and the second end of the elastic member is connected to the housing of the inhaler.

9. The button assembly according to claim 8, wherein the elastic member is a spring, the second assembly portion is shaped to be adapted to an inner diameter of the spring, and the second assembly portion is in interference fit with the spring.

10. The button assembly according to claim 1, wherein the inhaler comprises:

a first component and a second component, wherein the first component and the second component are configured such that when the second component rotates relative to the first component in a second direction, the second component is capable of moving away from the first component to a preloaded position, and wherein the at least one arm is arranged partially around the first component and/or the second component, and when the second component moves to the preloaded position, the at least one arm slides relative to an outer peripheral surface of the second component, such that the distal end of the at least one arm moves close to the housing of the inhaler.

11. The button assembly according to claim 10, wherein the at least one arm comprises a connecting portion pivotally connected to the first component and/or the second component, such that when the button body is pressed, the at least one arm pivots around the connecting portion.

12. The button assembly according to claim 10, wherein the distal end of the at least one arm comprises a bearing portion extending radially inwards from a main body thereof, the bearing portion being configured to abut against the second component when the first arm and the second arm slide relative to the outer peripheral surface of the second component.

13. The button assembly according to claim 10, wherein the distal end comprises a limiting protrusion arranged adjacent to the bearing portion and protruding from a bearing surface of the bearing portion, the limiting protrusion being configured to prevent the second component from rotating in the second direction when the bearing portion abuts against the second component.

14. The button assembly according to claim 13, wherein when the bearing portion abuts against the second component, the limiting protrusion tangentially contacts the second component to prevent the second component from rotating in the second direction.

15. The button assembly according to claim 3, wherein the pressuring force is related to a frictional force between each of the at least one arm and a second component, a magnitude of the frictional force being between 1 N and 6 N.

16. The button assembly according to claim 2, wherein the pressuring force is related to an elastic force of the elastic member acting on the button body, a magnitude of the elastic force being between 2 N and 8 N.

17. The button assembly according to claim 12, wherein when the second component moves to the preloaded position, the bearing portion is configured to be disengaged from the second component to release the second component when the button body is pressed.

18. The button assembly according to claim 17, wherein the button assembly further comprises a further elastic member, the further elastic member being configured to store energy when the second component moves away from the first component, and wherein when the bearing portion is disengaged from the second component, the second component moves toward the first component to a triggered position under the action of the further elastic member.

19. The button assembly according to claim 1, wherein the at least one arm has a second assembly hole at the proximal end, and the button body has a third assembly portion for fitting with the second assembly hole.

20. An inhaler, comprising:
a spray assembly; and
the button assembly according to claim 1, the button assembly being configured to be pressed to actuate the spray assembly to spray a liquid.

* * * * *